United States Patent [19]

Urton

[11] 3,954,967

[45] May 4, 1976

[54] METHOD OF PRODUCING MICROCOLLOIDAL AQUEOUS EMULSIONS OF UNSATURATED ORGANIC INSECTICIDAL COMPOUNDS

[75] Inventor: John T. Urton, Prairie Village, Kans.

[73] Assignee: Vanguard Chemical Company, Inc., Kansas City, Mo.

[22] Filed: Apr. 10, 1974

[21] Appl. No.: 459,673

Related U.S. Application Data

[62] Division of Ser. No. 169,248, Aug. 5, 1971, Pat. No. 3,813,345.

[52] U.S. Cl. ................................. 424/81; 424/78; 424/80; 424/192; 424/193; 424/257; 424/258; 424/270; 424/291; 424/300; 424/306; 424/331; 424/346; 424/352; 424/354; 424/363

[51] Int. Cl.$^2$ ................... A61K 31/78; A01N 9/20; A01N 9/30

[58] Field of Search ................ 424/78, 80, 81, 300, 424/306

[56] References Cited
UNITED STATES PATENTS 2,134,158   10/1938   Volck ............................... 252/312

OTHER PUBLICATIONS
Chemical Abstracts, Vol. 71, (1969), p. 128756j.

*Primary Examiner*—V. D. Turner
*Attorney, Agent, or Firm*—Lowe, Kokjer, Kircher, Wharton & Bowman

[57] ABSTRACT

A method of reducing the micelle size of an aqueous emulsion of an unsaturated organic compound utilizes an ionic pumping action to achieve micelle division. The resin utilized is selected on the basis of the presence in the molecular chain of a high number of sites which can accept a positive ion to cause the molecule to assume an overall charge. A gross emulsion is first formed utilizing a sufficient quantity of surfactant so that an excess is present to assure surfacating of the newly formed micelles upon division of the micelles of the initial emulsion. The resin is equilibrated utilizing a compound capable of donating positive ions to the resin molecule to cause the molecule to assume a charge of the same sign as the sign of the charge on the emulsion micelles. The resulting increased charge in the emulsion results in division of the micelles into micelles of a smaller size. The resin pumping action can be continued until the micelles of the emulsion are characterized by an inability to reflect light of a visible wavelength.

14 Claims, 3 Drawing Figures

METHOD OF PRODUCING MICROCOLLOIDAL AQUEOUS EMULSIONS OF UNSATURATED ORGANIC INSECTICIDAL COMPOUNDS

This is a division of prior application Ser. No. 169,248, filed Aug. 5, 1971, now U.S. Pat. No. 3,813,345.

The invention also provides for a method of killing insects wherein a microemulsion of an unsaturated organic compound having insecticidal properties is prepared in the manner set forth above. An additional step is the inclusion of a chelating agent for the calcium ions which are present in the basil membrane of an insect. This allows the emulsion micelles of the insecticide to penetrate through the insect.

The invention relates to the formation of aqueous emulsions and, more particularly, to a method of forming an aqueous emulsion having a reduced micelle size and to a method of utilizing emulsions of a decreased micelle size to increase the efficacy of biologically active compounds.

In many instances it is desirable to utilize an aqueous emulsion of an organic compound rather than dissolve the compound in an organic solvent. The ability to substitute an aqueous emulsion for an organic solvent is, however, limited by the size of the emulsion micelles. Where micelle size is critical, an emulsion cannot be satisfactorily substituted for a solution because the emulsion micelles are much larger in size than the molecules of a solution. For example, with water insoluble biologically active compounds, efficacy is directly proportional to the quantity of molecules available for reaction. Manifestly, if an aqueous emulsion could be provided wherein the emulsion micelles were of a size approaching that of molecules, the aqueous emulsion could be utilized with efficacy approaching that possible with an organic solvent. Additionally, while there are many obvious advantages in using a water base system, including availability and ease of handling, one of the most important considerations is the ecological impact. In recent years some biologically active compounds useful as herbicides, fungicides, and insecticides have been substantially limited in use or banned completely because of their harmful effects on the soil, the atmosphere, and mammalian toxicity. Often, however, the aforementioned harmful effects are attributable not to the active compound itself, but to the organic solvent, such as petroleum distillate, which is the solvent used to extract the compound.

While there have been previous attempts to form microemulsions wherein the micelle size is greatly reduced, these have been limited to the formation of gels which, when diluted out, broke to cloudy emulsions. While this in itself would prevent such a system from being useful with biologically active compounds on a large scale, another limitation of the microemulsion gels is the presence of a large excess of surfactant in the interphase which could cause phytotoxicity.

It is therefore an object of the present invention to provide a method of preparing emulsions of unsaturated organic compounds wherein sufficiently dilute concentrations of both the organic compound and any organic solvent in which it may be dissolved are possible so as to avoid the disadvantages associated with organic solvents and active compounds.

As a corollary to the above object, an important aim of the invention is to provide a method of preparing aqueous emulsions wherein the emulsion micelles are of a size approaching that of molecules in solution whereby the emulsion is similar in both physical properties and chemical activity to a true solution.

An important aim of this invention is also to provide a method of preparing an emulsion wherein the emulsion micelles are of a sufficiently small size that no Tyndell beam effect is observable in the visible light range thus evidencing the small size of the micelles.

An important object of this invention is to provide a method of forming an emulsion wherein the emulsion micelles are of a reduced size, as set forth in the above object, and the presence of excess surfactant in the external phase is avoided thus avoiding any possible harmful effects such as phytotoxicity from the excess surfactant.

Another object of the invention is to provide a method of forming an emulsion of biologically active compounds wherein a protective resin covering increases the stability of the compound and the protective covering is biodegradible so as not to interfere with the efficacy of the compound.

An objective of the invention is also to provide a method of forming aqueous emulsions wherein the presence of a resin material in the external phase of the emulsion prevents freezing far below the freezing point of water.

Another one of the objectives of my invention is to provide a method for preparing aqueous emulsions of biologically active compounds wherein the presence of a resinous compound which is utilized to reduce the micelle size of the emulsion results in better adhesion of the active compound to plants as a result of the close van der Waals' forces which are established with the plant cutin.

As a corollary to the above objective, another important object of the invention is to improve the adhesion of biologically active compounds to plants, and to simultaneously improve the adhesion of the active compound to an insect coming in contact therewith as a result of the formation of strong association bonds between the resin and the proteinaceous chitin or exoskeleton of the insects to thereby assure removal of the active compound from the plant by the insect.

It is also an aim of the present invention to provide a method for preparing aqueous emulsions wherein the emulsion micelles are of a substantially reduced size and this reduction in size is achieved by physiochemical effects thereby eliminating the need for expensive mechanical equipment.

Still another object of the invention is a method of preparing aqueous emulsions of unsaturated organic compounds wherein the micelle size of the emulsion is substantially reduced and wherein this reduction in size is achieved without chemical change of the organic compound.

An important objective of the present invention is to provide a method of preparing aqueous emulsions of biologically active compounds wherein the efficacy of the compounds is greatly increased over that possible with ordinary gross emulsions as a result of the increased penetrability of the emulsion micelles of a reduced size and the increased geometric surface area which is available for reaction.

As a corollary to the above object, this invention has as one of its objectives, the provision of a method of preparing aqueous emulsions of biologically active compounds wherein the efficacy of the compounds is increased to such an extent that the quantity of the compound utilized can be reduced thereby reducing the total cost and any possible adverse effects attributable to the compound.

Still another corollary to the object second above is to provide a method of increasing the efficacy of biologically active compounds whereby known compounds which have a lower level of activity but are also less likely to be harmful can be substituted for more active but potentially more harmful compounds.

Yet another object of this invention is a method of preparing an aqueous emulsion of biologically active compounds wherein the emulsion micelles are of a greatly reduced size, thereby resulting in increased efficacy of the compounds to a point where extraction of the compounds with potentially harmful organic solvents, such as petroleum distillate, can be avoided by extracting the compounds with less harmful solvents, such as alcohol.

It is also an aim of this invention to provide a method of preparing aqueous emulsions of organic compounds as described in the foregoing objects, which method is applicable to a large number of compounds, for example biologically active compounds formed from oleo resinous and natural carboxylic chemicals, chlorinated hydrocarbons, water insoluble phenolics, carbamates, quinone and quinoline hydrocarbons, thiol hydrocarbons; benzene and analine water insoluble dies; water insoluble aromatic oils; and water insoluble antioxidants.

An important object of this invention is also to provide a method of preparing microemulsions of organic compounds wherein a resinous pumping action is utilized to decrease the size of the emulsion micelles and wherein the presence of the resin increases the stability of the compound as a result of the protection from alkali and acid hydrolysis, as well as oxidation, which the resin affords.

Figures 1, 2, 3:
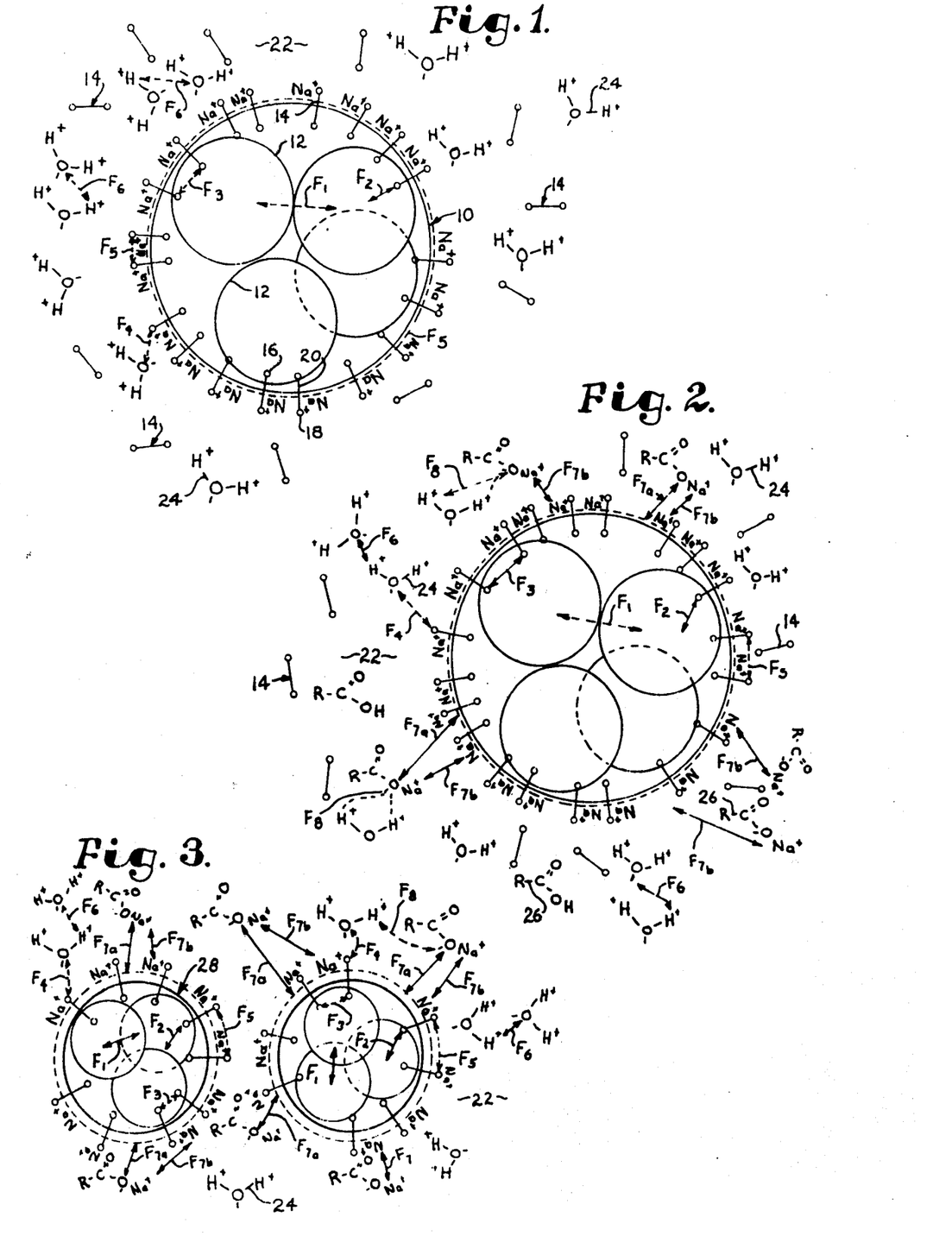

Another reason for the ineffectiveness of certain known biologically active compounds is that they are so reactive, either in solution or in an ordinary emulsion that they react with the environment before they actually enter a living organism which they are intended to act upon. It is therefore, another very important object of this invention to provide a method of forming an emulsion of biologically active compounds wherein the compound is protected from reaction with its environment by a resinous coating thereby greatly increasing the efficacy of the compound against the living organism on which it is intended to act.

An aim of this invention is also to provide a method of reducing the micelle size of aqueous emulsions without utilizing heat and thereby avoiding possible deleterious effects of the latter upon the internal emulsion phase.

This invention has, as another important aim, the provision of a method of reducing the micelle size of aqueous emulsions wherein the resulting microemulsions can be diluted out to very small concentrations without danger of breaking the emulsion thereby making the microemulsion system widely applicable for use with biologically active compounds.

It is also an important object of this invention to provide a method of killing insects wherein the efficacy of an insecticide is greatly increased by incorporating in the insecticide a chelating agent for the calcium ions present in the basil membrane of an insect thereby preventing these ions from blocking passage of the insecticide through this membrane.

A further aim of this invention is to provide a method of reducing the micelle size of aqueous emulsions of organic compounds to achieve superior penetration through wood for protecting live wood against insects and disease and for protecting dead wood against insects and deterioration in general.

BACKGROUND OF THE INVENTION

It has been reported (Schulman and Montague, Annals of the New York Academy of Science, Vol. 92, p. 336 (1961)) that it is necessary to produce negative interfacial tension between the emulsion micelles (internal phase) and the external phase (water) of an aqueous emulsion in order to achieve division of the micelles into micelles of a smaller size.

This negative interfacial tension has been defined in terms of the equation:

$$\gamma_i = \gamma_{o/w} - \pi \qquad (A)$$

where $\gamma_i$ = interfacial surface tension $\gamma_{o/w}$ = oil-water interfacial tension in the absence of a surfactant $\pi$ = spreading pressure of the surfactant at the oil-water interface Manifestly, either an increase in $\pi$ or a decrease in $\gamma_{o/w}$ will result in a negative value for $\gamma_i$ thus resulting in division of the emulsion micelles into micelles of a smaller size.

The present invention is best understood when equation A is expanded to describe in greater detail the forces which affect the value of $\gamma_i$. This expanded equation is represented as follows:

$$\gamma_i = (F_4 + F_6 - F_5) - (F_2 + F_1 - F_3) \qquad (B)$$

The forces $F_1$ through $F_6$ are represented schematically in FIG. 1 of the drawing wherein an emulsion micelle comprising the internal phase of an emulsion is designated generally by the numeral 10. The emulsion micelle is comprised of molecules of a hydrocarbon 12 which is water insoluble. The hydrocarbon 12 is represented by four small circles enclosed within a large circle and it is to be understood that the smaller circles are merely representative of the presence of the hydrocarbon and are not intended to indicate hydrocarbon molecules. Disposed around the outer periphery of the micelle 10 are a plurality of surfactant molecules 14. Each molecule 14 is comprised of a lipophilic end 16, a hydrophilic end 18, and a connecting chain 20 (FIG. 1). The lipophilic end 16 is soluble in the hydrocarbon 12 and the hydrophilic end 18 is soluble in the external aqueous phase which is represented generally by the numeral 22 and is comprised of a plurality of water molecules 24. A certain number of surfactant molecules 14, which have not yet found their way into the internal phase are also present in the external phase 22. In general, the surfactant molecules 14 may be of the nonionic, cationic or anionic type although it is preferable, as will be explained in greater detail hereinafter, to utilize a nonionic surfactant in combination with a small quantity of an anionic surfactant. Assuming the anionic surfactant is in the form of a sodium salt, the sodium ions will migrate toward the negative charge layer, which is thought to be a static charge, surrounding the micelle 10 and indicated by a broken line in FIGS. 1–3.

Referring again to equation B and to FIG. 1, the forces $F_1$ through $F_6$ are defined as follows:

$F_1 = HC_{ch}$ = cohesive force between the hydrocarbon molecules $F_2 = (S_{lp} \cdot HC_{ah})$ = adhesive attraction between the lipophilic end of the surfactant and the molecules of the hydrocarbon $F_3 = LP_{ch}$ = cohesive force between the lipophilic ends of the surfactant molecules $F_4 = (S_{hp} \cdot W_{ah})$ = adhesive attraction between the hydrophilic ends of the surfactant and the water molecules $F_5 = S_{hpch}$ = cohesive force between the hydrophilic ends of the surfactant molecules $F_6 = W_{ch}$ = cohesive force between the water molecules Transferring the above representations for $F_1$ through $F_6$ to equation B yields an equation:

$$\gamma_i = [(S_{hp} \cdot W_{ah}) + W_{ch} - S_{hpch}] - [(S_{lp} \cdot HC_{ah}) + HC_{ch} - S_{lpc}] \quad (C)$$

for the interfacial tension of an aqueous emulsion.

Prior attempts to reduce the micelle size of aqueous emulsions have, in part, been directed to adding large quantities of a nonionic surfactant with a low hydrophilic-lipophilic balance number. This lowers the factor $S_{hp} \cdot W_{ah}(F_4)$ in equation (C) and causes the overall factor of $\gamma_{o|w}$ (equation B) to be reduced. This causes $\gamma_i$ to assume a negative value and results in further micelle division. Since surfactants of this type are largely water insoluble, dilution of the emulsion is not possible and the technique can be used successfully only where a gel is an acceptable end product. Another disadvantage of utilizing a large excess of such a surfactant is that the surfactant molecules eventually become so crowded around the outside of the micelle that compaction occurs and the factor $S_{lpch}(F_3)$ dominates all others thereby preventing $\gamma_i$ from assuming a negative value and limiting the extent to which further reduction in micelle size can occur.

Still another known technique for reducing the micelle size of an emulsion is the application of heat. This can be utilized when the forces of compaction prevent further micelle division by the addition of more surfactant. Heat causes the van der Waals' forces to be temporarily broken and the value of $S_{hp} \cdot W_{ah}(F_4)$ in equation (C) to be reduced to give $\gamma_i$ a negative value and the emulsion micelles to undergo further division. This technique cannot be utilized with many compounds, however, because of the danger of decomposition from heating. Thus, most biologically active compounds are exempt from this procedure.

A third known method of reducing the micelle size of an emulsion is to introduce medium chain length fatty acids or alcohols into the emulsion. This tends to break or damp the van der Waals' forces, decreasing the values of $S_{hpch}(F_5)$ and $S_{lpch}(F_3)$ in equation (C). This technique is also limited in the extent to which it can reduce the micelle size and is not applicable to dilute aqueous emulsions because of the water insolubility of the fatty acids and alcohols used.

To avoid the disadvantages of the prior art methods discussed above and yet achieve a dilute aqueous emulsion of an unsaturated organic compound characterized by emulsion micelles of a size approaching that of molecules in solution, it has been found that a polyanionic or polycationic water soluble resinous compound can be utilized as a "pumping agent." To achieve micelle size reduction without encountering the limiting factor of compaction as discussed above, the resinous compound is introduced to form a relatively stationary external phase charge situation. The resin thereby achieves a reduction in the interfacial tension without actually becoming a part of the interface between the internal phase (emulsion micelles) and the aqueous external phase.

Referring to FIG. 2 of the drawing, the emulsion micelle 10 is disposed in the aqueous external phase 22 as previously described with a plurality of surfactant molecules 14 surrounding the micelle 10. A quantity of a polyacrylic acid polymer represented by the formula $RCO_2H$ is disposed in the external phase 22, with each molecule of the polymer being designated by the numeral 26. It is to be understood, of course, that the formula $RCO_2H$ for the molecules 26 is only representative of the actual formula for the molecules which would have a molecular weight in the range of from 250,000 to 3,000,000 with an enormous number of COOH groups in each molecule. When NaOH is added to the emulsion the following reaction occurs:

with a loose association bond between the $Na^+$ ions and the negative oxygen of the $CO_2^-$ radical resulting in an overall negative charge on the repeating resin group $RCO_2$. As NaOH continues to be added more and more of the repeating groups in the polymer chain will become charged while the pH of the emulsion will remain relatively constant because of the $OH^-$ ions from the NaOH combining with the displaced $H^+$ ions from the resin to form water.

The resulting increased charge in the external phase of the emulsion will cause division of the micelle 10 as a result of the following forces. First, the repulsive charge forces $F_{7a}$ and $F_{7b}$ (FIG. 2) between the overall negatively charged resin molecules 26 and the negative charge layer surrounding the micelle 10, and the similar repulsive charge between the $Na^+$ ions associated with the polymer acid groups and the $Na^+$ ions which surround the micelle 10, act as a positive charge pressure which is a counter force to the water interfacial tension. Second, because of the attractive force $F_8$ between the polar water molecules 24 and the charged resin molecules 26, the former will tend to migrate toward the latter, thereby reducing the attraction between the water molecules 24 and any surfactant molecules 14 which are present in the external phase. This in turn frees the molecules 14 to enter the micelle 10 as a result of their lipophilic attraction for the latter. The result is an increase in the value of $S_{lp} \cdot HC_{ah}(F_2)$ (equations B and C above) which contributes to a negative value for $\gamma_i$. Third, the migration of $H_2O$ molecules 24 to the charged resin molecules 26 removes the former from the surface of the micelle 10 decreasing the value of $S_{hp} \cdot W_{ah}(F_4)$. Fourth, it is thought that the presence of the charged resin molecules 26 also decreases the factor $W_{ch}(F_6)$ which further lowers the value of $\gamma_i$.

With all of the various factors working to reduce $\gamma_i$, the latter assumes a negative value and the micelles 10 divide into micelles 28 of a smaller size as indicated in FIG. 3. Division will continue until the increased surface area of the micelles 28 causes the surface tension to increase until $\gamma_i$ reaches zero and equilibrium exists.

DETAILED DESCRIPTION OF THE INVENTION

It has been found that aqueous emulsions of water insoluble unsaturated organic compounds can be prepared wherein the emulsion micelles are of a size approaching that of the molecules in solution. By "unsaturated organic compounds" is meant compounds wherein one or more carbon atoms are unsaturated with hydrogen atoms either as a result of multiple bonding or the presence of a substitute group. The compounds may be either aliphatic or aromatic, but in either case it is necessary that the compound be soluble in a polar solvent and that there be an absence of any of the elements iron, copper, zinc and phosphorus in the molecule. The unsaturated compounds which can be most effectively utilized in the invention generally fall within the molecular weight range of approximately 120 to 600. Examples of compounds which can be utilized in the invention include the following: oleoresinous and natural carboxylic compounds such as pyrethrin, cinneramic acid, pyrethrosin, monocarboxylic acids, crysanthmic acid, allethrin, dimethrin, oil of terpentine, terpinene, terpineol, terpinol, geraniol esters, citrolellol, dipentene, sesquiterpenes, asafetida, and aspidium; chlorinated hydrocarbons such as perthane, chlorodane, aldrin, dyrene, isodhen, heptachlor, toxaphene, chlorobendazide, chloroanil, endrin, parachlorophenoxyacetate, dichlorophenoxy propionic acid, orthochlorobenzene, neotan, dichlorodiphenyltrichloroethane, rhothane, ovex, and dichlone; water insoluble phenolics such as thymol, thyme oil, thymolphthalein, thymoquinone, allylphenol, methyl resorcinol, resorcinol monoacetate, resorcyclic acid, piperonyl cyclonene, dimethylphthalate, and creslyic acid; carbamate compounds such as carbaryl 1-naphthyl N-methylcarbamate), benomyl methyl 1-butylcarbamoyl-2-benzimidazolecarbamate, methyl naphthyl carbamate, solan, thanite, isopropyl N-(3-chlorophenyl) carbamate, "MGK 264" ($C_{17}H_{23}O_2N$), oil of myrbane, and binapacryl; quinonine and quinoline type compounds such as 8-hydroxyquinoline, 5-hydroxynaphthalquinone, dichlone, quinoidine, quininone, quinoline, quinolinic acid, quinone, quinovin, anthraquinone, ethyoxyquin, diphacinone, and methyl eugenol; thiol type compounds such as thianaphthalene, thiazole, sulfathiazole, thioacetaldehyde, thiocreosol, thioglycerol, thiolutin antibiotic, thionalide, thionine, thiophene, thiosalcyclic acid, thiouracil, and thiobendazole; aromatic essential oils such as oil of citron, oil of cloves, oil of peppermint, sesamin, oil of wintergreen, lemonene, pine oil, oil of eucalyptus, oil of sassifras, oil of nutmeg, oil of mustard, oil of ginger, and citronella; water insoluble amines such as aminoacetanilide, aminoacetophenone, aminoacridine, aminoazotoluene, aminobenzenesulfonamide, aminobenzathiazole, 2-amino- 1,2-diphenylethanol, aminosalicyclic acid, and aminopterin; benzene and analine dyes such as tetraazobenzene-beta-naphthol, acridine, dimethylaminoazobenzene, anthracene, anthragallol, azobenzene, and 1,2-benzanthracene, and antioxidants such as betahydroxyanisole and betahydroxytoluene.

In carrying out the method of the present invention, the internal phase of an emulsion is first prepared in a polar solvent, utilizing a surfactant which is soluble in the polar solvent in a quantity of at least two parts by volume of the surfactant to one part by volume of the unsaturated organic compound of the type described above which is being emulsified. The surfactant used should be one which is capable of forming a microemulsion. Those skilled in the art will recognize that the following are known requirements of a surfactant capable of forming a microemulsion: a surfactant molecular chain length longer than the molecular chain length of the compound being emulsified, solubility of the surfactant in the compound being emulsified and vice versa, and an adhesive attraction of the surfactant for the compound being emulsified which is greater than the cohesive force between the molecules of the compound. Because of the use of a polar organic solvent and the desirability of a high aqueous dilution in the final emulsion the surfactant also should have a hydrophilic-lipophilic balance number of 11 or greater, and preferably within the range of 11 to 14.

While the quantity of surfactant utilized is not critical within a reasonable range, there should be a sufficient amount present in the initial emulsion to assure surfacation of all of the micelles upon division, and the quantity should not be so large as to result in compaction and limit micelle division, or result in excess surfactant being present in the external phase thus causing possible phytotoxicity. It has been found that at least two parts by volume of the surfactant to one part by volume of the compound to be emulsified should be used and that in general quantities in excess of a 4:1 ratio by volume should be avoided.

Examples of nonionic surfactants which can be utilized in the invention include the polyoxyethylene sorbitan esters of mixed fatty and resin acids as sold under the trademark "Atlox 8916T" by Atlas Chemical Industries, Inc. of Wilmington, Delaware, polysorbate 20 as sold under the trademark "Tween 20" by the Atlas company, polyoxyethylene 20 sorbitan monopalmitate as sold under the trademark "Tween 60" by the Atlas company, polyoxyethylene 20 sorbitan monooleate as sold under the trademark "Tween 80" by the Atlas company, polyoxyethylene 40 stearate as sold under the trademark "Myrj 52" by the Atlas company, polyoxyethylene 40 stearate as sold under the trademark "Myrj 525" by the Atlas company, polyoxyethylene 50 stearate as sold under the trademark "Myrj 53" by the Atlas company, polyoxyethylene esters of mixed fatty and resin acids as sold under the trademark "Renex 20" by the Atlas company, polyoxyethylene 20 palmitate as sold under the trademark "G-2079" by the Atlas company, polyoxyethylene 23 lauryl ether as sold under the trademark "Brij 35" by the Atlas company, polyoxyethylene 20 cetyl ether as sold under the trademark "Brij 58" by the Atlas company, polyoxyethylene 20 oleyl ether as sold under the trademark "Brij 98" by the Atlas company, polyoxyethylene 12 tridecyl ether as sold under the trademark "Renex 30" by the Atlas company, polyoxyethylene 15 tridecyl ether as sold under the trademark "Renex 31" by the Atlas company, polyoxyethylene 25 oxypropylene monostearate as sold under the trademark "G-2162" by the Atlas company, and polyoxyethylene alkyl amine as sold under the trademark "G-3780A" by the Atlas company.

Examples of anionic surfactants which can be utilized in the invention include those sold under the trademarks "Triton X-151" and "Triton X-152" by the Rohm & Haas Company of Philadelphia, Pa., both of which are blends of alkylaryl polyethers, a blend of a polyaryl polyether alcohol with an organic sulfonate such as sold under the trademark "Triton X-172" by the Rohm & Haas Company, a sodium salt of an alkylaryl polyether sulfonate such as sold under the trademark "Triton X-200" by the Rohm & Haas company, sodium salts of alkylaryl polyether sulfonates such as sold under the trademarks "Triton W 30" and "Triton 770" by the Rohm & Haas company, and a dioctyl sodium sulfosuccinate as sold under the trademark "Triton Gr-5" by the Rohm & Haas company.

Examples of cationic surfactants which can be utilized in the invention include the tertiary and quaternary water soluble amines, stearyl dimethyl benzyl ammonium chloride, a trialkyl tin complex having a high weight ratio of tertiary amine groups, benzalkonium chloride, amido alkyl amine oxides, alkyl dimethylamine oxides, and a hydrogenated tallow amine-steryl amine plus a vegetable amine as sold under the trademark "Trymeen HTA 15". The amphoteric surfactant sold under the trademark "Triton OS 15" by the Rohm & Haas company, and which is a sodium salt of an alkylaryl polyether sulfonate can also be utilized.

In general, it is preferable to use a nonionic or cationic surfactant or a combination of a nonionic and an anionic. Because of possible phytotoxicity, the concentration of anionic surfactant should generally not exceed 20% by volume of the total quantity of surfactant. The fact that an anionic surfactant carries a positive ion, such as sodium, which is available for migration to the micelle interface to increase the positive charge on the micelles, makes it advantageous to use a small quantity of the anionic surfactant in combination with a nonionic. The cationic surfactants are used where additional protection from acid destruction is desired. It is also known that some cationic surfactants are germicidal compounds and these can be utilized to increase the overall killing power of the microcolloidal emulsion when a biologically active compound is being emulsified. The preferred surfactant in all cases where it is compatible with the system is Tween 80 as identified above. When it is desired to combine an anionic surfactant with Tween 80, Triton X-151 is preferred.

Organic polar solvents which can be utilized in the invention include the $C_8$ and lower alcohols, dimethyl sulfoxide, diethyl sulfoxide and methyl pyrrole. When it is desired to incorporate a calcium chelating agent in the emulsion, as will be discussed in greater detail hereinafter, dimethyl sulfoxide is very useful since it can serve in the dual role of solvent and chelating agent. In general, however, methyl alcohol is the preferred solvent because of its lower cost. It may also be desirable in certain instances to combine a relatively small volume of dimethyl sulfoxide with one of the other polar solvents for optimum results.

The quantity of the solvent utilized is, of course, dependent upon the concentration of the compound being emulsified. In order to achieve a microcolloidal emulsion the unsaturated organic compound should comprise no more than approximately 4% by volume of the total emulsion with the polar solvent comprising from 10% to 25% of the total volume. It is not essential that the resinous compound be added to the internal phase, prepared as described above, at this point in time but instead the resin can be added to the microemulsion after dilution of the internal phase with water. It is preferable, however, to add a first quantity of resin to the internal phase prior to dilution with water and a second quantity of either the same or a different resin to the initial gross emulsion after the latter is formed. The resinous compound should be characterized by a high number of positive ion accepting sites, such as carboxyl (e.g. acrylic) or —CON— (e.g. pyrrolidone) groups, in each molecule of the compound. In addition to having a high number of positive ion accepting sites which can react with a positive ion donor, such as an acid or a base, to form a charged resin molecule, the resinous compound should be water soluble.

Examples of resinous compounds which can be utilized in the present invention include polyacrylic acid polymers, including ammoniacal forms of the latter, carboxyvinyl polymers, pyrrolidone polymers, and naturally occurring resinous compounds such as gum arabic, agar-agar, and gum tragacanth. By a high number of positive ion accepting sites is meant that the molecule should have at least as many such sites as the naturally occurring resinous compounds mentioned above and preferably at least one such site in each repeating monomer of the molecule as in the case of polyacrylic acid and pyrrolidone polymers.

The selection of the resinous compound is to be based upon the charge assumed by the emulsion micelles. In some instances it is found that the micelles assume an overall negative charge in which case a resin having a carboxyl or equivalent group is utilized. Upon addition of an equilibrating base or amine to an aqueous solution of the resin, the resin molecule will assume an overall negative charge and the liberated hydrogen and hydroxyl ions will combine to form water. This charge will increase in magnitude as equilibration continues and more of the monomer groups assume a negative charge. This charge acts as a positive force charge (7a in FIGS. 2 and 3) against the emulsion micelles and causes the latter to divide, as previously explained. When a base is used in the equilibration, the cation from the base forms a loose association bond with the carboxyl group, giving the resin molecule an overall negative charge, but also resulting in a partial positive charge on the associated cation. The positive charge exerts a further repulsive force (7b in FIGS. 2 and 3) against any cations which have migrated to the micelle interphase, as previously explained. This further enhances the pumping action of the resin.

When it is necessary that the resin assume an overall positive charge, rather than a negative charge, a resinous compound having a pyrrolidone or equivalent group is utilized. When an inorganic acid is added to an aqueous solution of such a compound, the acid hydrogen ion combines with the nitrogen of the pyrrolidone group to give the resin an overall positive charge. This charge also increases in magnitude as equilibration continues thereby effecting micelle division.

The quantity of resin added at this point can vary over a considerable range. It has been found, however, that the quantity should generally not exceed approximately 0.1% by weight of the final microemulsion since no further micelle division is observed above this level. The optimum quantity is approximately 0.01% by weight of the final microemulsion. Lesser quantities result in larger micelle size in the final microemulsion with little effect noted when the initial quantity of resin added is less than 0.005% by weight of the final microemulsion.

To assure that the resinous compound goes into the solution of the internal phase, it is desirable to partially equilibrate the resin with either an acid or a base (depending upon whether the positive ion accepting group is pyrrolidone or carboxyl) to adjust the pH for maximum solution. For example, the polyacrylic acid resins are partially equilibrated with NaOH to a pH of about 6.0 – 6.8 before adding the resin to the emulsion. The pyrrolidone resins are pH adjusted to about 8.0 before addition.

It is also desirable in many instances to incorporate in the internal phase an antioxidant to prevent the formation of peroxides. This is of value in preventing destruction of the compound being emulsified, particularly where the compound is biologically active and the microemulsion is placed in field use. The antioxidant also prevents the formation of peroxides in certain of the lower chain length vinyl and acrylic resins which could otherwise cause further polymerization of the resin. The antioxidant betahydroxytoluene is preferred with acrylictype resins and the antioxidant betahydroxyanisole is preferred with pyrrolidone-type resins. Examples of other antioxidants which can be used in the invention include N,N'-diphenyl-paraphenylonediamine, 2,2'-methylene/bis-(4 methyl-6-tertiarybutyl-phenol), N-phenyl-beta-naphthylamine, 4,4'-dimethoxydiphenylamine, parahydroxyanisole, N-butyl-para-aminophenol, N,N'-di(secondary butyl) paraphenylenediamine, hydroxyquinone, catechol, alpha-naphthol, and phenothiazine. The antioxidant should normally be present in a ratio of at least one part antioxidant to 100 parts (by weight) of the unsaturated organic compound being emulsified. The antioxidant is preferably selected so that a microcolloidal emulsion of this compound will also be formed.

After the internal phase of the yet to be formed emulsion is completed by the addition of the unsaturated organic compound, the antioxidant, the surfactant, and an initial quantity of resin to the polar solvent, all as explained in detail above, the internal phase is diluted to at least 70% by volume with water. Next, in those cases where a microemulsion of an insecticide is being prepared, it has been discovered that it is highly advantageous to incorporate a calcium chelating agent in the emulsion. The presence of calcium ions in the basil membrane of insects acts as a defense mechanism to block the entry of any foreign molecules. By including a calcium chelating agent, such as EDTA, in the emulsion of the insecticide the calcium ions can be "tied up" and the emulsion micelles are free to pass through the basil membrane of the insect.

In general, coordination compounds of the bi-, tri-, hexa-, or poly-dentate type such as diethylenetriamine and EDTA may be utilized to sequester the calcium ions. Salts such as sodium heparin and sodium citrate can also be used. As previously mentioned, the solvent dimethyl sulfoxide can also serve as the calcium chelator. EDTA is the preferred chelating agent and even when DMSO is used as a solvent it is sometimes desirable to include a quantity of EDTA. The quantity of EDTA or other chelating agent added to the emulsion is not critical within a reasonable range although it should generally comprise a quantity equal to at least 10% by weight of the quantity of unsaturated organic compound being emulsified and not greater than 30% by weight of this compound. The EDTA is normally dissolved in one ml of distilled and deionized water before it is added to the emulsion.

At this point, an additional quantity of a resinous compound of the type described above is added to the emulsion. This may be the same resin as added prior to the formation of the initial emulsion or another resin of the same type which will further enhance the charge forces acting on the micelles after equilibration. The quantity of resin added at this stage of the procedure can again vary over a wide range. Most desirably, however, the quantity should not exceed approximately 0.1% by weight of the final microemulsion, since no benefits are obtained with higher levels, and is preferably approximately 0.05% by weight of the final microemulsion. In the event the resin addition prior to formation of the initial gross emulsion is omitted, the quanity of resin added at the present stage could exceed the optimum levels noted above. Quantities less than the optimum result in larger micelle size in the final microemulsion with little effect noted when this second resin addition is in a quantity of less than 0.005% by weight of the final microemulsion.

The resin present in the emulsion is now equilibrated using a compound capable of donating positive ions to the positive ion accepting sites of the resin to cause these sites to assume a charge of the same sign as the sign of the charge on the micelles of the initial gross emulsion. When the positive ion accepting site is a carboxyl group, a strong base such as sodium hydroxide or ammonium hydroxide, or an amine such as triethanolamine, monoethanolamine, diisopropanolamine, dodecylamine, di(2-ethylhexyl amine) or Ethomeen C25 (a product of Armour Industrial Chemical Co. of Chicago, Ill.) is utilized in the equilibration. When the positive ion accepting site is a pyrrolidone group, hydrochloric acid should be utilized in the equilibration.

Sodium hydroxide is the preferred equilibrating medium for carboxyl groups whenever the emulsion is at least 75% by volume water. In the event that glycerol or ethylene glycol is added to the emulsion, or a concentration of methyl alcohol of 25% or greater is present, $NH_4OH$ is the preferred equilibrating medium. For systems using ethanol or isopropyl alcohol in concentrations of 10% by volume or greater, an amine such as diisopropanolamine or triethanolamine should be utilized for optimum results.

The quantity of the equilibrating medium added is calculated on the basis of the quantity of resin utilized and how much of the equilibrating compound will be needed to equilibrate a given quantity of resin. The following are exemplary quantities in milliliters of selected equilibrating compounds which would be utilized to neutralize an emulsion containing 0.2% by weight of a polyacrylic acid polymer of the type previously described:

| Final pH after equilibration | 10% NaOH | 28% $NH_4OH$ | 50% D.I.P.A.[1] | 50% T.E.A.[2] | 50% M.E.A.[3] |
|---|---|---|---|---|---|
| 4.0 | 0.21 | 0.10 | 0.2 | 0.3 | 0.04 |
| 4.5 | 0.45 | 0.16 | 0.5 | 0.6 | 0.11 |
| 5.0 | 0.83 | 0.24 | 0.8 | 0.9 | 0.23 |
| 5.5 | 1.13 | 0.36 | 1.2 | 1.4 | .37 |
| 6.0 | 1.66 | 0.52 | 1.6 | 1.8 | 0.55 |
| 6.5 | 2.21 | 0.61 | 2.0 | 2.3 | 0.75 |

-continued

| Final pH after equilibration | 10% NaOH | 28% NH₄OH | 50% D.I.P.A.[1] | 50% T.E.A.[2] | 50% M.E.A.[3] |
|---|---|---|---|---|---|
| 7.0 | 2.75 | 0.69 | 2.4 | 2.7 | 0.98 |
| 7.5 | 3.35 | 0.76 | 2.8 | 3.3 | 1.18 |
| 8.0 | 3.84 | 0.83 | 3.3 | 5.0 | 1.38 |
| 8.5 | 4.35 | 0.89 | 4.2 | 8.0 | 1.50 |
| 9.0 | 4.50 | 0.99 | 6.6 | 16.0 | 1.65 |

[1]D.I.P.A. diisopropylamine
[2]T.E.A. triethylamine
[3]M.E.A. monoethylamine

When the compound being emulsified is biologically active, such as a pesticide, insecticide or fungicide, it is important that there be no substantial change in the pH of the emulsion during the equilibration. Any change greater than approximately 2 pH units would be substantial and could result in denaturing of the biologically active compound. The pH is maintained within a range of 2 pH units by selecting the equilibrating compound so that the equilibrating reaction does not release substantial quantities of free H⁺ or OH⁻ ions into the emulsion, and controlling the quantity of the compound to avoid excess amounts which would release excess quantities of H⁺ or OH⁻ ions.

As a final step, the microemulsion is diluted with water to an aqueous concentration of at least 95% by volume. While as previously noted, the aqueous phase can comprise a smaller fraction of the total emulsion, a 95% to 97% by volume aqueous phase is preferred in most instances.

The following examples are indicative of the above-described procedure. In each of the examples the compound being emulsified is an insecticide, thus the optional step of adding a calcium chelating agent is included in each procedure.

Example I

One gram (1.1 ml) of allethrin is dissolved in 10 ml of methyl alcohol. To the resulting solution is added 0.01 gm of betahydroxytoluene antioxidant.

Next, 2 ml of polysorbate 80 are added to the solution with gentle mixing. A polyacrylic acid polymer such as that sold by the B. F. Goodrich Chemical Co. of Cleveland, Ohio, under the trademark "Good-rite WS 801", and having a molecular weight of 250,000, in a quantity of 8 ml of a 1% by weight aqueous solution is equilibrated to a pH of 6.8 using dilute NaOH and then added to the above solution with gentle stirring.

The resulting internal phase for the microemulsion is then diluted with sufficient water to provide a total volume of 80 ml of the initial emulsion. A quantity of EDTA (0.1 gm) is dissolved in 1 ml of distilled and deionized water which is then added to the microemulsion. A total of 20 ml of a 0.5% by weight solution of carboxypolymethylene, the pH of which has been adjusted to approximately 6.0 by the addition of NaOH, is now added with mixing. While mixing, the polyacrylic acid and carboxypolymethylene are equilibrated by the addition of 15 ml of a 0.1% by weight solution of sodium hydroxide. Finally, the equilibrated microemulsion is diluted with water to a total of 1000 ml. The above procedure can be repeated using similar quantities of any of the exemplary compounds previously categorized as "oleoresinous and natural carboxylic compounds."

Example II

One gram of chlorodane is dissolved in 20 ml of methyl alcohol. To the resulting solution is added 0.1 gm of betahydroxytoluene. A total of 3 ml of an alkylaryl polyether alcohol-sulfonate surfactant, such as that sold under the trademark Triton X-151 by the Rohm & Haas Co. of Philadelphia, Pa., is then added to the solution.

Next, 8 ml of a 1% by weight aqueous solution of Good-rite WS 801 polyacrylic acid resin, which has been equilibrated to a pH of 6.8 as explained in Example I, is added with thorough mixing. Water is added to bring the total volume up to 80 ml. EDTA (0.1 gm in 1 ml of distilled and deionized water) is added to the resulting emulsion with thorough mixing. An additional quantity of resin, 20 ml of a 0.5% by weight aqueous solution of carboxypolymethylene, is now added.

The polyacrylic acid and carboxypolymethylene resins are now equilibrated with 15 ml of a 0.1% solution of sodium hydroxide. The equilibrated microemulsion is finally diluted to a volume of 1000 ml with water.

The foregoing procedure can be repeated utilizing similar quantities of any of the exemplary compounds previously categorized as "chlorinated hydrocarbons."

Example III

One gram of thymol is dissolved in 15 ml of methyl alcohol. As an antioxidant, 0.01 gm of betahydroxyanisole is added to the solution. A total of 2.0 ml of concentrated benzalkonium chloride are now added to the solution with mixing.

Fifteen ml of a 1% aqueous solution of N-methyl-2-pyrrolidone copolymer, which has been pH adjusted with NaOH to 8.0, is now added to the solution. A sufficient quantity of water to provide a total volume of 95 ml is then added to the previously prepared internal phase. One-tenth gram of EDTA is now added to the emulsion. A total of 5 ml of a 90% aqueous solution of polyvinylpyrrolidone is added to supplement the methylpyrrolidone previously added.

To equilibrate the pyrrolidone resins, 20 ml of a 0.1% by weight solution of HCl is added until the final pH of the emulsion is approximately 6.8. The equilibrated microemulsion is diluted with water to a total volume of 1000 ml.

The foregoing procedure can be repeated using similar quantities of any of the exemplary compounds previously categorized as "water insoluble phenolics."

Example IV

Example III is repeated using 10 ml of dimethylsulfoxide as a solvent for the thymol in place of the methyl alcohol. This allows the EDTA to be omitted since the DMSO is itself a calcium chelating agent.

Example V

One gram of 1-naphthyl N-methyl carbamate (available under the trademark "Sevin" from the Union Carbide Corporation of New York, N.Y.) is dissolved in 30 ml of methyl alcohol and 0.01 gm of betahydroxytoluene is added to the solution. A total of 3 ml of polysorbate 60 is then added to the solution to complete the internal emulsion phase.

A polyacrylic acid polymer of the same type as utilized in Example I and similarly adjusted in pH is utilized to form a 1% by weight aqueous resin solution. Eight ml of this resin solution are added to the internal phase referred to above subsequent to which sufficient water is added to bring the total volume to 80 ml and form the aqueous emulsion. EDTA (0.1 gm) is now added to the emulsion menstruum.

Next, a second quantity of resin, 20 ml of a 0.5% by weight aqueous solution of carboxypolymethylene which has been pH adjusted to approximately 6.0 is added to the emulsion with mixing.

Equilibration is achieved with the addition of 15 ml of a 0.1% by weight solution of NaOH. Finally, the emulsion is diluted to a total volume of 1000 ml with water.

The foregoing procedure can be repeated using similar quantities of any of the exemplary compounds previously categorized as "carbamate compounds."

Example VI

To one gram of 8-hydroxyquinoline, a total of 3.3 ml of a blend of polysorbate 80 (3.0 ml) and the anionic surfactant identified in Example II as being sold under the trademark Triton X-151 (0.3 ml), plus 25 ml of methyl alcohol are added simultaneously. It is highly desirable to dissolve the hydrocarbon in the surfactant and the solvent simultaneously for optimum results. To the resulting solution is added 0.03 gm of betahydroxytoluene.

Next, a polyacrylic acid polymer of the type identified in Example I and pH adjusted as described in the latter example, is added to the solution in a quantity of 7 ml of a 1% aqueous solution after which water is added to bring the total volume to 80 ml and form the emulsion. The calcium chelating agent EDTA (0.1 gm) is now added to the emulsion.

A second quantity of resin, 20 ml of a 0.5% by weight aqueous solution of carboxypolymethylene, which has been pH adjusted to approximately 6.0 with NaOH, is added to the emulsion menstruum with thorough mixing. Equilibration is achieved with 25 ml of 0.1% by weight solution of NaOH. Finally, sufficient water is added to bring the total volume to 1000 ml.

The foregoing procedure can be repeated using similar quantities of any of the exemplary compounds previously categorized as "quinonine and quinoline type compounds."

Example VII

To one gram of Sudan Red dye, which is available from the General Aniline & Film Corporation of New York, N.Y., is added 30 ml of methyl alcohol to achieve solution. Betahydroxytoluene is then added to the resulting solution in a quantity of 0.02 gm.

Next 5 ml of polysorbate 80 are added with mixing. Ten ml of a 1% by weight aqueous solution of the polyacrylic acid polymer Good-rite WS 801, as identified in Example I, which has been pH adjusted to 6.8 as explained in the referenced example, is added to the solution.

Water is added to the above-prepared internal phase to bring the total volume to 85 ml and form the initial emulsion. EDTA, prepared according to Example I, is added in a quantity of 1 ml. Fifteen ml of an aqueous solution of carboxypolymethylene (containing 0.075 gm of the resin) is then added. Eleven ml of a 1% by weight solution of NaOH is utilized to equilibrate the resin with the final pH of the emulsion being 7.5. The final equilibrated emulsion is diluted with water to a volume of 1000 ml.

Ethyl alcohol can be substituted for methyl alcohol in the above procedure with equally satisfactory results. The procedure can also be repeated using similar quantities of any of the exemplary compounds previously categorized as "benzene and analine dyes."

Example VIII

One gram of oil of cloves is dissolved in ethyl alcohol by adding the latter to the former. Betahydroxytoluene (0.01 gm) is added to the resulting solution. Six ml of polysorbate 60 are then added.

The polyacrylic acid polymer Good-rite WS 801, as identified in Example I, is added in a quantity of 4 ml after pH adjustment to 6.8. Water is added next to bring the total volume to 80 ml. One ml of EDTA, prepared as explained in Example I is then added to the microemulsion. Twenty ml of an aqueous solution of carboxypolymethylene (containing 0.1 gm of the resin) are added and equilibration is achieved with 15 ml of a 0.1% by weight aqueous solution of NaOH. Final dilution to 1000 ml is achieved by adding water.

The above procedure can be repeated using similar quantities of any of the exemplary "essential oils" previously mentioned.

Example IX

One gram of thiabendazole is dissolved in 10 ml of methyl pyrrole. Betahydroxyanisole (0.01 gm) is added to the resulting solution. Next, 3 ml of concentrated benzalkonium chloride are added with mixing.

To the above solution of the internal phase, 12 ml of a 1% aqueous solution of methyl pyrrolidone, which has been pH adjusted to 8.0 with hydrochloric acid, are added. Dilution to 80 ml with water forms the initial emulsion, and 1.0 ml of a 0.1 gm aqueous solution (distilled and deionized water) of EDTA is added as a calcium chelating agent.

Next, 20 ml of polyvinylpyrrolidone (90% by weight aqueous solution) is added and the resin is equilibrated with 20 ml of a 0.4% by weight solution of HCl. The resulting microemulsion is diluted to a total volume of 1000 ml with water.

The above procedure can be repeated using similar quantities of any of the exemplary "thiol type compounds" previously mentioned.

Example X

One gram of aminoacridine is added to 25 ml of isopropyl alcohol with 0.01 gm of betahydroxytoluene present as an antioxidant. Four ml of polysorbate 60 are then added to complete the internal phase of the emulsion.

The polyacrylic acid polymer Good-rite WS 801 as identified in Example I (pH equilibrated to 6.8) is then added in a quantity of 6 ml. Water is added to a total of 80 ml to form the initial emulsion. EDTA, in a quantity of 0.3 gm in 1 ml of distilled and deionized water is added next. A solution of 0.1 gm of carboxypolymethylene in 20 of water (pH 6.0) is incorporated into the emulsion as an additional resin pumping agent.

The resins are equilibrated with 25 ml of a 0.1% by weight solution of $NH_4OH$. The final pH is 8.0. After equilibration, the resulting microemulsion is diluted to a total volume of 1000 ml with water.

The above procedure can be repeated using similar quantities of any of the exemplary compounds previously categorized as "water insoluble amines."

Example XI

Mercuric resourcinol acetate, 1 gm, is dissolved in 5 ml of methyl pyrrole with 0.01 gm of betahydroxyanisole being added as an antioxidant. To the resulting solution, 4 ml of concentrated benzalkonium chloride is added.

Methyl pyrrolidone is the resin pumping agent utilized and 15 ml of a 1% by weight aqueous solution of pH=80 incorporated in the solution of the internal phase. Water is added to bring the total volume to 95 ml. EDTA, 0.2 gm dissolved in 2 ml of distilled and deionized water, is added to the resulting emulsion as is polyvinylpyrrolidone in a quantity of 5 ml of a 90% by weight aqueous solution. The resins are equilibrated with 20 ml of a 0.1% by weight solution of HCl. Finally, the microemulsion is diluted to a total volume of 1000 ml with water.

The following tests were run to determine the micelle size of the microcolloidal emulsions prepared according to the teachings of the present invention. In each case the optical refraction (O.R.) was measured using photomultiplier cells, a preamplifier unit, and registered on a standard millivolt meter. Five ml standard quartz cuvettes were used as emulsion receptacles during the optical measurements.

First of all, emulsions of ten different unsaturated organic compounds were prepared without the addition of the resinous compound and equilibration of the latter with an acid or a base (see Examples XII – XVI, infra). The resulting emulsions were clear although they were found to reflect a Tyndell beam in the visible light range as reported in Table 1 below.

Table 1

Optical Refracton (Visible Spectrum) of Microemulsions Prepared Without Utilization of Resin Pumping Principle

| Emulsion | O.R. (%) 1:100 dilution | O.R. (%) 1:1000 dilution |
|---|---|---|
| 1. Pyrethrin | 2.0 | 0.2 |
| 2. Allethrin | 3.3 | 0.3 |
| 3. Sevin | 2.7 | 0.25 |
| 4. 8-hydroxyquinoline | 3.4 | 0.36 |
| 5. Juglone | 3.2 | 0.29 |
| 6. Perthane | 3.7 | 0.33 |
| 7. Rhothene | 3.6 | 0.34 |
| 8. Sudan Red | 1.8 | 0.14 |
| 9. Clove Oil | 5.2 | 0.46 |
| 10. Oil of Wintergreen | 4.2 | 0.39 |

The results reported in Table 2 below indicate the effects of the resin pumping action on the micelle size and the ability of micelles to reflect light.

Table 2

Optical Refraction (Visible Spectrum) of Microemulsions Prepared Utilizing Resin Pumping Action

| Emulsion | O.R. (%) Before Equilibration 1:100 dilution | O.R. (%) Before Equilibration 1:1000 Dilution | O.R. (%) After Equilibration 1:100 Dilution |
|---|---|---|---|
| 1. Pyrethrin | 2.36 | .55 | .35 |
| 2. Allethrin | 3.54 | .65 | .37 |
| 3. Sevin | 3.05 | .60 | .42 |
| 4. 8-hydroxyquinoline | 3.78 | .72 | .33 |
| 5. Juglone | 3.57 | .60 | .35 |
| 6. Perthane | 4.05 | .63 | .36 |
| 7. Rhothane | 4.0 | .69 | .33 |
| 8. Sudan Red | 2.2 | .50 | .34 |
| 9. Clove Oil | 5.55 | .80 | .32 |
| 10. Oil of Wintergreen | 4.60 | .85 | .35 |

| | O.R. (%) After Equilibration 1:1000 Dilution | Calculated* O.R. (%) Attributable to Resin Alone (1:100 dilution) |
|---|---|---|
| 1. | .35 | .36 |
| 2. | .37 | .24 |
| 3. | .43 | .35 |
| 4. | .34 | .38 |
| 5. | .36 | .37 |
| 6. | .35 | .35 |
| 7. | .34 | .40 |
| 8. | .35 | .40 |
| 9. | .35 | .35 |
| 10. | .34 | .40 |

*column 1, Table 2 less column 1, Table 1

As indicated above, the optical refraction of each emulsion dropped back to the value expected for the resin alone after equilibration. To confirm that all of the refraction indicated in columns three and four in fact was attributable to the resin itself, to each of the emulsions was added 1% by weight of NaCl. This caused precipitation of the resin. Following centrifugation and decanting of the supernatant fractions from each emulsion, the supernatants were again tested for optical refraction and all values found to be zero when corrected against a water blank. To prove the presence of the emulsion micelles, each of the samples from which the resin had been precipitated was tested against a standard U.V. light source (Blak-Ray UVL-21, 115 v, 60 cycle, 0.12 amps) and found in every case to exhibit some refraction.

To determine the stability of the microemulsions prepared according to the method of the present invention, four different compounds were prepared utilizing 0.1% by weight active ingredient in a total emulsion volume of 1000 ml. The percentage of effectivity lost is based upon spectroscopic examination in the ultraviolet as well as insect minometer tests for potency. As indicated in the following table the microcolloidal emulsions (MCE) prepared according to the invention were much more stable than ordinary emulsions.

Table 3

| | Percent Effectivity Lost After One Month | | | |
|---|---|---|---|---|
| | | Rm. Temp. | | 120°F. |
| Active Ingredient | MCE Rm. Temp. | Ordinary Emulsion (Std.) | MCE 120° F. | Ordinary Emulsion (Std.) |
| Pyrethrin | 6 | 58 | 12 | 78 |
| Allethrin | 8 | 63 | 15 | 86 |
| Sevin | 14 | 97 | 22 | 100 |
| Oil of Cloves | 5 | 30 | 6 | 70 |

Tests run to determine the extent of permeability in insects of microcolloidal emulsions prepared according to the method of the present invention were also run. A 0.01% by weight aqueous microemulsion of pyrethrin was prepared according to the method of the present invention and an ordinary emulsion of the same compound at the same strength was also prepared. A second control was prepared using an ordinary emulsion plus dimethyl sulfoxide (DMSO) in a 10% by weight concentration. As those skilled in the art will appreciate, DMSO is generally regarded as the most highly penetrable solvent known. Grasshoppers (15 for each group) were chosen for this penetrability test. All insects tested were dipped in the respective emulsions for three seconds duration and then allowed to stand for three hours to permit the chemical to penetrate the exoskeleton. The chitinous exoskeleton was then removed to expose the underlying membrane and dipped in a 4% solution of NaOH. The purple Formazan that results is an indication of the pyrethrin concentration in the membrane. The purple Formazan pyrethrin alkylate is extracted from the tissue by placing the latter in test tubes containing 75% isopropyl alcohol and 25% glycerol with heating to a gentle boil. The extract was then placed in a photometer and the optical density (O.D.) read.

The results were compared against the standard prepared by killing an insect, removing the exoskeleton, dipping the basil membrane into an ordinary emulsion of pyrethrin and extracting the pyrethrin to obtain the purple Formazan sample which was placed in the photometer and given a value of 4+. The results are stated in Table 4 below.

Table 4

| | Purple Formazan Test of Insect Penetrability (4+= optimum O.D. value) | | |
|---|---|---|---|
| Insect No. | Microcolloidal Emulsion - Pyrethrin O.D. | Control Emulsion Pyrethrin O.D. | Control Emulsion Pyrethrin plus DMSO O.D. |
| 1 | 2+ | trace | 1+ |
| 2 | 1+ | trace | 2+ |
| 3 | 2+ | neg. | 1+ |
| 4 | 2+ | neg. | 1+ |
| 5 | 2+ | trace | trace |
| 6 | 1+ | neg. | 1+ |
| 7 | trace | neg. | trace |
| 8 | 1+ | trace | 2+ |
| 9 | 2+ | 1+ | 1+ |
| 10 | 2+ | trace | trace |
| 11 | 3+ | neg. | 1+ |
| 12 | 1+ | neg. | trace |
| 13 | trace | trace | trace |
| 14 | 2+ | trace | 1+ |
| 15 | 2+ | trace | trace |
| Average | 1+ – 2+ | neg. – trace | 1+ |

From the data tabulated above it is apparent that the microemulsion prepared according to the present invention gave far better penetration than either the ordinary emulsion or the emulsion plus the solvent dimethyl sulfoxide.

To determine the penetrability of emulsions prepared according to the present invention through wood, the following test was run. A 0.01% by weight aqueous microemulsion of allethrin and a 0.01% by weight aqueous microemulsion of Sudan Red dye were prepared according to the present invention. Similar quantities of the allethrin and dye were dissolved in the following solvents: ether, methyl alcohol, chloroform, terpentine, benzene and dimethyl sulfoxide (DMSO). One ml of each solution or emulsion was injected into a block of live wood approximately 1 inch thick and 5 inches – 7 inches in diameter and allowed to penetrate for one hour. A value of 4+ was given to the maximum area penetrated and a value of 3+ as given for penetration of an area three-fourths as large as the maximum area, and so on. The results are tabulated in Table 5 below.

Table 5

Wood Block Penetration
4+ = maximum area penetrated
Column A = allethrin
Column B = Sudan Red dye
tr. = trace
neg. = negative penetration

| Block | Ordinary Emulsion A | Ordinary Emulsion B | Micro-emulsion A | Micro-emulsion B | Ether A | Ether B | CH$_3$OH A | CH$_3$OH B | Chloroform A | Chloroform B | Terpentine A | Terpentine B |
|---|---|---|---|---|---|---|---|---|---|---|---|---|
| 1 | neg. | neg. | 4+ | 3+ | 1+ | 1+ | tr. | tr. | tr. | tr. | neg. | neg. |
| 2 | neg. | neg. | 3+ | 4+ | 1+ | tr. | tr. | 1+ | neg. | tr. | neg. | neg. |
| 3 | neg. | neg. | 4+ | 4+ | 1+ | 1+ | tr. | tr. | neg. | tr. | neg. | neg. |
| 4 | neg. | neg. | 4+ | 4+ | tr. | 1+ | tr. | tr. | neg. | tr. | neg. | neg. |
| 5 | neg. | neg. | 4+ | 3+ | 1+ | tr. | tr. | 1+ | tr. | 1+ | neg. | neg. |
| 6 | neg. | neg. | 4+ | 4+ | 1+ | 1+ | tr. | tr. | neg. | tr. | neg. | neg. |
| 7 | neg. | neg. | 3+ | 4+ | 1+ | 1+ | tr. | 1+ | neg. | tr. | neg. | neg. |
| 8 | neg. | neg. | 4+ | 4+ | 2+ | 1+ | tr. | 1+ | neg. | 1+ | neg. | neg. |
| 9 | neg. | neg. | 4+ | 4+ | 1+ | 1+ | tr. | tr. | tr. | tr. | neg. | neg. |
| 10 | neg. | neg. | 4+ | 4+ | 1+ | 1+ | tr. | tr. | neg. | tr. | neg. | neg. |

| Block | Benzene A | Benzene B | DMSO A | DMSO B |
|---|---|---|---|---|
| 1 | tr. | tr. | 2+ | 1+ |
| 2 | tr. | 1+ | 1+ | 1+ |
| 3 | tr. | 1+ | 1+ | 1+ |
| 4 | tr. | tr. | 1+ | 1+ |
| 5 | tr. | 1+ | 2+ | 1+ |
| 6 | tr. | 1+ | 1+ | 1+ |
| 7 | tr. | 1+ | tr. | tr. |
| 8 | tr. | 1+ | 1+ | tr. |
| 9 | tr. | 1+ | 1+ | 1+ |
| 10 | tr. | tr. | 2+ | 1+ |

Actual insect kill tests were run to compare the killing effectiveness of microcolloidal emulsions (MCE) of insecticidal compounds prepared according to the invention with ordinary emulsions (control) of the same compound. The chemicals Sevin, allethrin, and pyrethrin were tested and in each case a microemulsion was prepared according to the procedures set forth in Examples V, I and I, respectively. The control emulsions were prepared using the similar quantities of the compounds. In each case readings were taken at the end of the first, second, fifth and twenty-fourth hours and in determining the experimental values for L.D.$_{50}$ corrections were made for any shifts in viability of the insects that occurred after the initial readings. The results are summarized in Tables 6 – 11.

Table 6

Effectivity of Sevin on hymenoptera (Yellow Jacket Hornet)

| Dilution | Total No. Insects (MCE) | Total No. Insects (Control) | % Viable 24 Hrs. (MCE) |
|---|---|---|---|
| 1:1000 | 10 | 10 | 0 |
| 1:4000 | 10 | 10 | 0 |
| 1:10000 | 10 | 10 | 20 |
| 1:20000 | 10 | 10 | 90 |
| 1:40000 | 10 | 10 | 100 |
| 1:60000 | 10 | 10 | 100 |

| Dilution | % Lethal 24 Hrs. (MCE) | % Viable 24 Hrs. (Control) | % Lethal 24 Hrs. (Control) |
|---|---|---|---|
| 1:1000 | 100 | 80 | 20 |
| 1:4000 | 100 | 100 | 0 |
| 1:10000 | 80 | 100 | 0 |
| 1:20000 | 10 | 100 | 0 |
| 1:40000 | 0 | — | — |
| 1:60000 | 0 | — | — |

LD$_{50}$ experimental for Sevin MCE = 1:15000 dilution
LD$_{50}$ experimental for Sevin control = 1:500 dilution (approx.)

The above test with Sevin was repeated using orthoptera (German cockroach), diptera (housefly) and coleoaptera (mealy worm beetle larva). The dilution values found for both the MCE and the control emulsion are given in Table 7.

Table 7

Effectivity of Sevin on Selected Insects – LD$_{50}$

| Insect | LD$_{50}$ Dilution Ratio MCE | LD$_{50}$ Control |
|---|---|---|
| Orthoptera | 1:35000 | 1:2500 |
| Diptera | 1:17500 | 1:2500 |
| Coleoaptera | 1:70000 | 1:3250 |

Table 8

Effectivity of D-Trans Allethrin on Orthoptera (German Cockroach)

| Dilution | Total No. Insects (MCE) | Total No. Insects (Control) | % Viable 24 Hrs. (MCE) |
|---|---|---|---|
| 1:1000 | 50 | 50 | 0 |
| 1:4000 | 50 | 50 | 0 |
| 1:10000 | 50 | 50 | 0 |
| 1:20000 | 50 | 50 | 34 |
| 1:40000 | 50 | 50 | 94 |
| 1:60000 | 50 | 50 | 93 |

| Dilution | % Lethal 24 Hrs. (MCE) | % Viable 24 Hrs. (Control) | % Lethal 24 Hrs. (Control) |
|---|---|---|---|
| 1:1000 | 100 | 0 | 100 |
| 1:4000 | 100 | 96 | 4 |
| 1:10000 | 100 | 100 | 0 |
| 1:20000 | 66 | 100 | 0 |
| 1:40000 | 6 | 100 | 0 |
| 1:60000 | 2 | 100 | 0 |

LD$_{50}$ experimental for Allethrin MCE   1:24,500 dilution
LD$_{50}$ experimental for Allethrin Control   1:2500 dilution The above test with allethrin was repeated using hymenoptera (yellow jacket hornet), diptera (housefly), and coleoptera (mealy worm beetle larva). The dilution values found for both the MCE and the control emulsion are tabulated below.

Table 9

Effectivity of Allethrin on Selected Insects - $LD_{50}$ Dilution Ratio

| Insect | $LD_{50}$ MCE | $LD_{50}$ Control |
|---|---|---|
| Hymenoptera | 1:17500 | 1:650 |
| Diptera | 1:50000 | 1:4750 |
| Coleoptera | 1:17500 | 1:2500 |

Table 10

Effectivity of Pyrethrin on Diptera (Housefly)

| Dilution | Total No. Insects (MCE) | Total No. Insects (Control) | % Viable 24 Hrs. (MCE) |
|---|---|---|---|
| 1:1000 | 50 | 50 | 0 |
| 1:4000 | 50 | 50 | 0 |
| 1:10000 | 50 | 50 | 0 |
| 1:20000 | 50 | 50 | 0 |
| 1:40000 | 50 | 50 | 0 |
| 1:60000 | 50 | 50 | 0 |

| Dilution | % Lethal 24 Hrs. (MCE) | % Viable 24 Hrs. (Control) | % Lethal 24 Hrs. (Control) |
|---|---|---|---|
| 1:1000 | 100 | 0 | 100 |
| 1:4000 | 100 | 68 | 32 |
| 1:10000 | 100 | 96 | 4 |
| 1:20000 | 100 | 100 | 0 |
| 1:40000 | 100 | 100 | 0 |
| 1:60000 | 100 | 100 | 0 |

$LD_{50}$ experimental for Pyrethrin MCE = could not be calculated although greater than 1:60000
$LD_{50}$ experimental for Pyrethrin Control = 1:2750

The above test with pyrethrin was repeated using hymenoptera (yellow jacket hornet), orthoptera (German cockroach) and coleoptera (mealy worm beetle larva). The dilution values found for both the MCE and the control emulsion are tabulated below.

Table 11

Effectivity of Pyrethrin on Selected Insects - $LD_{50}$ Dilution Ratio

| Insect | $LD_{50}$ MCE | $LD_{50}$ Control |
|---|---|---|
| Hymenoptera | 1:16500 | 1:1750 |
| Orthoptera | 1:50000 | 1:2750 |
| Coleoptera | 1:25000 | 1:2500 |

From the data in Tables 6 through 11 it is apparent that the kill effectivity of microcolloidal emulsions prepared according to the present invention far exceeds that of conventional emulsions. In every case, the dilution ratio for the MCE is much higher than for the control.

Tests were also run to determine whether or not the increased efficacy of biologically active compounds, such as insecticides, prepared as microemulsions according to the present invention, is accompanied by an increase in mammalian toxicity.

The known toxic level for both Sevin and allethrin insecticides is between 0.5 and 1.5 gm/kg of body weight. In a 1:1000 dilution emulsion (0.1% by weight active ingredient) three gallons of the emulsion would be required to provide the MLD. Based on the fact that an insecticide prepared as a microemulsion would normally be diluted at from 1:10000 — 1:20000, and the fact that a dog could not conceivably consume even three gallons of an insecticide, one quart of the 1:1000 emulsion was selected for the toxicity tests. This volume of insecticide is the maximum feasible which a dog could contact since it is the amount which adheres to a dog when it is completely immersed in the emulsion. It is to be understood, however, that the actual quantity of the active ingredient could normally not be expected to exceed from one-tenth to one-twentieth of the quantity applied in the 1:1000 test dilution, even if the animal were completely immersed.

Fifteen test dogs and fifteen control dogs were completely immersed in 0.1% by weight aqueous emulsions of allethrin. One emulsion was prepared according to the invention (test) and the other was an ordinary emulsion (control). The dogs in each group were observed for general appearance, grooming habits, sneezing or coughing, feeding habits and intake, appearance of feces, appearance of eyes and mucus membranes, nervousness, measured water intake, urinalysis, white and red blood counts. Except for the fact that two animals in the control group contacted pneumonia, which was cleared up with medication, all animals in both groups were normal in every respect after some initial excitement and generally poor appearance from the dunking.

The same test was repeated using 15 test animals and 15 control animals with 0.1% emulsions of the insecticide Sevin being utilized in place of allethrin with similar results.

To further confirm that the biologically active microcolloidal emulsions of the invention do not result in increased mammalian toxicity tests were run on mice given intraperitoneal injections of emulsions containing insecticidal compounds. The average weight of some 240 mice used as a test group and another 240 mice used as a control group was 20 gm. Using the known value for the toxicology of allethrin of 0.5 – 1.5 gm/kg of body weight, the calculated lethal dose for a 20 gm mouse, utilizing a 1% aqueous emulsion, would be from 1 to 3 gm.

Twelve groups of 20 mice each (20 test mice plus 20 control mice) were injected intraperitoneally with varying amounts of 1% aqueous emulsions of pyrethrin. The test groups were injected with a microemulsion prepared according to the present invention and the control groups were injected with an ordinary emulsion.

Table 12

Toxicity to Mice of Ordinary Emulsion (Control) and Microcolloidal Emulsion (MCE) of Sevin Injected Intraperitoneally

| Group No. (20 animals each) | Dosage (gm) I.P. Injection | No. Animals MCE Viable | No. Animals MCE Dead | No. Animals Control Viable | No. Animals Control Dead |
|---|---|---|---|---|---|
| 1 | 3 | 0 | 20 | 0 | 20 |
| 2 | 2 | 3 | 17 | 4 | 16 |
| 3 | 1 | 12 | 8 | 11 | 9 |
| 4 | 0.9 | 18 | 2 | 17 | 3 |
| 5 | 0.8 | 20 | 0 | 19 | 1 |
| 6 | 0.7 | 19 | 1 | 20 | 0 |
| 7 | 0.6 | 20 | 0 | 20 | 0 |
| 8 | 0.5 | 20 | 0 | 20 | 0 |
| 9 | 0.4 | 20 | 0 | 20 | 0 |
| 10 | 0.3 | 20 | 0 | 20 | 0 |
| 11 | 0.2 | 20 | 0 | 20 | 0 |
| 12 | 0.1 | 20 | 0 | 20 | 0 |

$LD_{50}$ experimental for MCE = 1+ gm dosage
$LD_{50}$ experimental for Control = 1+ gm dosage
MLD experimental for MCE = 0.7 gm dosage
MLD experimental for Control = 0.8 gm dosage When the above test was repeated substituting 1% aqueous microcolloidal and ordinary emulsions of allethrin for the Sevin the results summarized below were observed:

LD$_{50}$ experimental for MCE = 1+ gm dosage
LD$_{50}$ experimental for Control = 1+ gm dosage
MLD experimental for MCE = 0.7 gm dosage
MLD experimental for Control = 0.8 gm dosage Thus in both instances the values for the LD$_{50}$ and the MLD of the microemulsion and the ordinary emulsion were essentially the same and within known toxic levels for these chemicals. There is, therefore, no increased toxicity to mammals from the microcolloidal emulsions of the invention and the increased efficacy of the emulsified compound is clearly specific for the insects, fungi, etc, which it is desired to kill.

As indicated by the data in the above tables, when the method of the present invention is employed with biologically active compounds, such as insecticides, the efficacy of the compound can be greatly increased without an increase in mammilian toxicity. The increased efficacy is attributable to smaller emulsion micelle size, greater penetrability, increased stability, greater specificity as a result of protection from reaction with the environment, and greater adhesion to both the plants protected and the insects to be killed. It will thus be appreciated that incorporation of the resinous compound into the emulsion serves not only as an effective "pumping agent" to reduce micelle size, but when the emulsion is applied to a plant or other living body and the aqueous phase evaporates, the resin is left as a protective shield for the micelles. The increased effectiveness allows for smaller quantities of the active compound and its organic solvent to be utilized while also making available many relatively "safe" compounds heretofore having found only limited use because of their low kill effectivity. The method of the invention also makes economically feasible the extraction of many useful compounds with relatively harmless solvents such as alcohol, because of the substantially lower quantity of the compounds which need be used.

The method of the present invention can also be used to protect cut wood from deterioration in general and from insects by using an emulsion of a protective compound to saturate the wood. Because of the increased effectiveness and penetrability of any active compound microcolloidalized by the inventive process, superior results are obtained with smaller quantities of the compound. The method of the invention can also be employed with water soluble dyes to impart color to wood and wood products. Still another use of the invention method is in the inoculation of animals by applying microcolloidal emulsion to the skin rather than by injection.

ALTERNATIVE FORM OF THE INVENTION

In those cases where the resinous covering which protects the emulsion micelles is either undesirable or unnecessary, the efficacy of an unsaturated organic compound of the type described on page 12 and having biological activity can be greatly increased utilizing the following method. Examples of compounds which can be utilized in this alternative procedure include all of those compounds listed on pages 13 and 14 which are biologically active as insecticides, fungicides, etc.

In carrying out this alternative method, the internal phase of an emulsion is first prepared in a polar solvent, utilizing a surfactant which is soluble in the polar solvent in a quantity of at least eight parts by volume of the surfactant to one part by volume of the unsaturated organic compound. The surfactant should again be one capable of forming a microemulsion as discussed previously in conjunction with the preferred embodiment of the invention. The various surfactants previously listed as exemplary and set forth on page 15 can be utilized in this alternative procedure. Examples of polar solvents which can be utilized include those previously listed on page 17.

As with the procedure previously described, it is preferable to incorporate an antioxidant into the internal phase to guard against oxidation of the biologically active compound. Examples of antioxidants which can be utilized include those listed on page 20. the antioxidant should normally be present in a ratio of at least one part antioxidant to 100 parts (by weight) of the compound being emulsified.

After the internal phase of the yet to be formed emulsion is completed by the addition of the unsaturated organic compound, the antioxidant, and the surfactants, as explained above, the internal phase is diluted to at least 70% by volume with water. The resulting emulsion is characterized by emulsion micelles of a reduced size although the micelles do show some reflection of light in the visible spectrum.

To "tie up" the calcium ions in the basil membrane of an insect, a chelating agent is added to the emulsion at this stage. EDTA is the preferred chelating agent, although other known calcium chelators, including those specified on page 21 can be utilized. The quantity of the chelating agent utilized should be at least 10% and not greater than 30% by weight of the quantity of the compound being emulsified.

As a final step, the emulsion prepared as set forth above is preferably diluted to at least 95% by volume water. While as previously noted, the aqueous phase may comprise as little as 70% by volume water, in most cases a more dilute emulsion is desirable.

While an emulsion prepared by the alternative method described above is not as stable against acid, alkali and heat deterioration because of the absence of the protective resin, it has been found that such an emulsion exhibits superior penetrability approaching that reported in Tables 4 and 5, infra. Efficacy of the emulsions prepared according to this alternative procedure has also been found to be greatly superior to ordinary emulsions and approaches that reported in Tables 6 – 11. This alternative method of preparing an emulsion of a biologically active compound is particularly adapted for use where the emulsion is intended to be used as an injection systemic for protection of large plants such as trees.

The example set forth below are indicative of the procedure to be followed when practicing the alternative form of the invention described above.

Example XII

One gram (1.1 ml) of pyrethrin is dissolved in 10 ml of methyl alcohol. To the resulting solution is added 0.01 gm of betahydroxytoluene antioxidant.

Next, 8 ml of polysorbate 80 are added to the solution with gentle mixing. The resulting internal phase is then diluted with water to form the emulsion with the quantity of water added being sufficient to provide a total volume of 80 ml. One-tenth gram of EDTA dissolved in 1 ml of distilled and deionized water is then added to the emulsion. Finally, the emulsion is diluted with water to a total volume of 1000 ml.

The above procedure can be repeated using similar quantities of any of the exemplary compounds previously categorized as "oleoresinous and natural carboxylic compounds."

Example XIII

One gram of the insecticide sold under the name "Perthane" (100%) by the Rohm & Haas Co. of Philadelphia, Pennsylvania and based on 1,1-dichloro-2,2-bis(para-ethylphenyl)-ethane is dissolved in 20 ml of methyl alcohol. To the resulting solution is added 0.1 gm of betahydroxytoluene. A total of 10 ml of an alkylarly polyether alcohol-sulfonate surfactant, such as that sold under the trademark Triton X-151 by the Rohm & Haas Co. of Philadelphia, Pennsylvania is then added to the solution.

Water is added to bring the total volume to 80 ml and form the emulsion. EDTA (0.1 gm in 1 ml of distilled and deionized water) is added resulting the reeulting emulsion with thorough mixing. Finally, the emulsion is diluted to a total volume of 1000 ml with water.

The foregoing procedure can be repeated utilizing similar quantities of any of the exemplary compounds previously categorized as "chlorinated hydrocarbons."

Example XIV

One gram of methylated resorcinol is dissolved in 15 ml of methyl alcohol. As an antioxidant, 0.01 gm of betahydroxyanisole is added to the solution. A total of 8.0 ml of concentrated benzalkonium chloride are now added to the solution with mixing.

Next, a sufficient quantity of water to provide a total volume of 95 ml is added to form the emulsion and one-tenth gram of EDTA is introduced. Finally, the emulsion is diluted to a total volume of 1000 ml with water.

The foregoing procedure can be repeated using similar quantities of any of the exemplary compounds previously categorized as "water insoluble phenolics."

Example XV

One gram of chlorophenyl carbamate is dissolved in 30 ml of methyl alcohol and 0.01 gm of betahydroxytoluene. A total of 10 ml of polysorbate 60 is then added to the solution to complete the internal emulsion phase. Next, sufficient water is added to bring the total volume to 80 ml and form the aqueous emulsion. The calcium chelating agent EDTA (0.1 gm) is introduced into the emulsion menstruum and as a final step the emulsion is diluted to a volume of 1000 ml with water.

The foregoing procedure can be repeated using similar quantities of any of the exemplary compounds previously categorized as "carbamate compounds."

Example XVI

To one gram of 8-hydroxyquinoline a total of 11 ml of a blend of polysorbate 80 (10 ml) and the anionic surfactant identified in Example II as being sold under the trademark Triton X-151 (1.0 ml) plus 25 ml of methyl alcohol are added simultaneously. It is highly desirable to dissolve the hydrocarbon in the surfactant and the solvent simultaneously for optimum results. To the resulting solution is added 0.03 gm of betahydroxytoluene.

To form the emulsion, water is added to bring the total volume to 80 ml and 0.1 gm of EDTA is included in the emulsion. Finally, sufficient water is added to bring the total water to 1000 ml.

The foregoing procedure can be repeated using similar quantities of any of the exemplary compounds previously categorized as "qunionine and quinoline type compounds."

SECOND ALTERNATIVE FORM OF THE INVENTION

It has also been discovered that polyacrylic acid polymers can be utilized to form highly stable pastes and powders of biologically active unsaturated organic compounds of the type previously described. The following described procedure is particularly adapted for use with those compounds which are commonly sold in powder or paste form and for which a ready market as a dilute aqueous emulsion does not exist. Surface active properties are imparted to a polyacrylic acid polymer by dual neutralization allowing the polymer to act as an emulsifier and stabilizer.

An aqueous solution of a polyacrylic acid polymer, is first prepared, preferably utilizing from 0.1 to 0.3% by weight of the polymer. The polymer is then partially equilibrated with an appropriate base, such as NaOH or $NH_4OH$, with the carboxyl groups of the polymer reacting with the base to form water and yield a substituted polymer molecule. Next, the polymer is farther equilibrated with an amine selected from the group consisting of "Ethomeen C25", triamylamine, triethylamine, and di-(2-ethylhexyl)amine. The amine reacts with the ureacted carboxyl groups to impart lipophilic properties to a portion of the polymer molecule.

Prepared separately is an "oil phase" by dissolving the unsaturated organic compound in a polar solvent, such as those listed on page 17. To this solution is added a nonionic surfactant that is soluble in the polar solvent. Thus, the surfactant should have a hydrophilic-lipophilic balance number of at least 11, and while any of the nonionic surfactants listed on page 15 can be utilized, polysorbate 80 is preferred in all cases. The quantity of surfactant utilized can vary from as little as 1 part by volume of surfactant to 5 parts by volume of the active compound when the final product is to be in powder form to 2 parts by volume of surfactant to 1 part of the compound when a concentrated emulsion is to be formed. At this point, the "oil phase" prepared as described above is combined with the aqueous solution of the polymer to form an aqueous emulsion of the unsaturated organic compound.

In the event l-naphthyl N-methyl carbamate is the compound being emulsified, and methyl alcohol is the solvent in which this compound is dissolved, it has been found desirable, just prior to combining the "oil phase" with the aqueous solution, to add to the oil phase the same amine used to partially equilibrate the polymer in a quantity equal to the quantity used in the polymer equilibration. Similarly, when l-naphthyl N-methyl carbamate is the compound being emulsified, and dimethyl sulfoxide is the solvent used to prepare the "oil phase," it is preferable to add to this phase, immediately prior to the combining step, triethylamine in a quantity equal to the quantity of amine used to equilibrate the polymer.

The emulsion itself may be utilized to apply the unsaturated organic compound in those cases where a relatively high concentration of the compound is desired. Concentrations in excess of 6% by weight of the active ingredient can be prepared in this manner and it is found that the biologically active compound exhibits three to four times the stability against light, acid, and alkali deterioration as an ordinary emulsion of the same compound.

When it is desired to convert the emulsion to a concentrated paste, a saline solution is added to the emulsion to precipitate the polymer complex of the active compound. The supernatant liquid is decanted and the resulting paste is normally from 30% – 35% by weight active ingredient. To convert the paste to a powder, the liquid is removed by evaporation or desiccation. In either paste or powder form, the final product can be easily reemulsified and is again three to four times as stable against light, acid, and alkali deterioration as an ordinary emulsion of the same compound.

The following example is illustrative of the above described alternative form of the invention.

Example XVII

Carboxypolymethylene (0.26 gm) is dissolved in 80 ml of water and then equilibrated with approximately 0.3 gm (dry) of NaOH. Next approximately 0.3 gm of Ethomeen C25 is added to complete equilibration. This completes the aqueous phase.

The oil phase is prepared by dissolving 10 gm of l-naphthyl N-methyl carbamate in 50 ml of methyl alcohol and adding 2 ml of polysorbate 80 surfactant. Before combining the aqueous and oil phases, 0.3 gm of Ethomeen C25 is added to the oil phase.

At this point, the two phases are combined to form the aqueous emulsion. Adequate mixing assures a good emulsion although homogenization equipment can be employed if desired. A 0.1 normal saline solution is added to the above prepared emulsion to precipitate out the polymer-complex of the l-naphthyl N-methyl carbamate. The supernatant liquid is decanted and the resulting paste is evaporated to a dry powder.

Having thus described the invention what is claimed as new and desired to be secured by Letters Patent is:

1. A method of reducing the micelle size of an aqueous emulsion of an unsaturated organic compound having insecticidal properties, said compound being characterized by solubility in an organic polar solvent, and an absence of the elements iron, copper, zinc and phosphorous, said method comprising the steps of:
   preparing the internal phase of said emulsion by adding a quantity of said compound along with a quantity of surfactant to an organic polar solvent,
   said compound being present in a quantity such that the volume of the compound relative to the volume of the subsequently formed emulsion is no more than approximately 4%, and said solvent being present in a quantity such that the volume of the solvent relative to the volume of the subsequently formed emulsion is from 10% to 25%,
   said surfactant being characterized by the ability to form a microemulsion which is soluble in said polar solvent and said surfactant being present in a quantity of at least approximately two parts by volume of said surfactant to one part by volume of said compound;
   diluting said internal phase to at least approximately 70% by volume water to form said emulsion;
   adding to said emulsion a quantity of a water soluble resinous compound to comprise at least approximately 0.005% by weight of the subsequently formed microemulsion characterized by the presence of a high number of positive ion accepting sites in each molecule of the resinous compound, there being at least one site in each repeating monomer of the molecule;
   equilibrating said resinous compound with a stoichiometric quantity of a compound capable of donating positive ions to said sites to cause the latter to assume a charge of the same sign as the sign of the charge on the emulsion micelle while maintaining a substantially constant pH in said emulsion;
   whereby the increased charge in the emulsion from the molecules of the resinous compound results in division of the emulsion micelles into micelles of a smaller size to form a microemulsion; and
   incorporating in the emulsion a chelating agent for the calcium ions present in the basil membrane of an insect to thereby increase the penetrability of said organic compound through said insect.

2. The method as set forth in claim 1, wherein said step of incorporating a chelating agent comprises utilizing dimethyl sulfoxide as the polar solvent for preparing said internal phase.

3. The method as set forth in claim 1, wherein said step of incorporating a chelating agent comprises adding to the emulsion a quantity of ethylenediaminetetraacetic acid.

4. A method of reducing the micelle size of an aqueous emulsion of an unsaturated organic compound having insecticidal properties, said compound being characterized by solubility in a polar solvent, and an absence of the elements iron, copper, zinc and phosphorous, said method comprising the steps of:

preparing the internal phase of said emulsion by dissolving a quantity of said compound in an organic polar solvent, adding a quantity of surfactant to the resulting solution, and mixing of the surfactant and the solution, said compound being present in a quantity such that the volume of the compound relative to the volume of the subsequently formed emulsion is no more than approximately 4%, and said solvent being present in a quantity such that the volume of the solvent relative to the volume of the subsequently formed emulsion is from 10% to 25%, said surfactant being characterized by the ability to form a microemulsion which is soluble in said polar solvent and said surfactant being present in a quantity of at least approximately two parts by volume of said surfactant to one part by volume of said compound;

adding to said internal phase a quantity of a water soluble resinous compound selected from the group consisting of polyacrylic acid and pyrrolidone polymers in a quantity of at least 0.005% by weight of the subsequently formed microemulsion;

diluting said internal phase to at least approximately 70% by volume water to form said emulsion;

adding to said emulsion a second quantity, comprising at least 0.005% by weight of the subsequently formed microemulsion, of said resinous compound; and equilibrating said resinous compound with a stoichiometric quantity of a compound capable of donating a positive ion to the acid radical of said polyacrylic acid or to the amide radical of said pyrrolidone to cause the radical to assume a charge of the same sign as the sign of the charge on the emulsion micelles, said equlibrating step comprising equilibrating said resinous compound with a compound selected from the group consisting of sodium hydroxide, ammonium hydroxide, triethanolamine, monoethanolamine, and diisopropanolamine when said resinous compound is a polyacrylic acid polymer, and wherein said equilibrating step comprises equilibrating said resinous compound with hydrochloric acid when said resinous compound is a pyrrolidone polymer, said equilibrating step including the step of maintaining a substantially constant pH in the emulsion, whereby the increased charge in the emulsion from the molecules of said resinous compound results in division of the emulsion micelles into micelles of a smaller size to form a microemulsion; and incorporating in the emulsion a chelating agent for the calcium ions present in the basil membrane of an insect to thereby increase the penetrability of said organic compound through said insect.

5. A method of reducing the micelle size of an aqueous emulsion of an unsaturated organic compound having insecticidal properties said compound being characterized by solubility in a polar solvent, and an absence of the elements iron, copper, zinc and phosphorous, said method comprising the steps of:

dissolving a quantity of said compound in a polar solvent;

said compound being present in a quantity such that the volume of the compound relative to the volume of the subsequently formed emulsion is no more than approximately 4%, and said solvent being present in a quantity such that the volume of the solvent relative to the volume of the subsequently formed emulsion is from 10% to 25%;

adding to the resulting solution a surfactant capable of forming a microemulsion which is soluble in the solution, in a quantity of at least approximately two parts by volume of said surfactant to one part by volume of said compound;

mixing said surfactant and the solution to form an internal phase;

adding to said emulsion a second quantity, comprising at least 0.005% by weight of the subsequently formed microemulsion, of a water soluble resinous compound characterized by the presence of a high number of positive ion accepting sites in each molecule of the resinous compound;

equilibrating said resinous compounds with a stoichiometric quantity of a compound capable of donating positive ions to said sites to cause the latter to assume a charge of the same sign as the sign of the charge on the emulsion micelles, while maintaining a substantially constant pH in the emulsion, whereby the increased charge in the emulsion from the molecules of the resinous compounds results in division of the emulsion micelles into micelles of a smaller size to form a microemulsion;

continuing said equilibrating step until the resulting micelles of a smaller size are characterized by an inability to reflect light of a visible wavelength; and incorporating in the emulsion a chelating agent for the calcium ions present in the basil membrane of an insect to thereby increase the penetrability of said organic compound through said insect.

6. The method as set forth in claim 5, wherein said organic compound comprises pyrethrin, said dissolving step comprises dissolving a quantity of said pyrethrin in methyl alcohol; and including the additional step of adding a quantity of betahydroxytoluene to the solution, said step of adding a first quantity of a resinous compound comprising adding a quantity of a polyacrylic acid polymer to said internal phase, said step of incorporating a chelating agent comprising adding a quantity of ethylenediaminetetraacetic acid to the emulsion, and said equilibrating step comprising adding a quantity of sodium hydroxide to the emulsion.

7. The method as set forth in claim 5, wherein said organic compound comprises l-naphthyl N-methyl carbamate, said dissolving step comprises dissolving a quantity of said l-naphthyl N-methyl carbamate in a solution of approximately 40% by volume dimethyl sulfoxide and approximately 60% by volume methyl alcohol, said step of adding a surfactant comprising adding a quantity of polyoxyethylene sorbitan monostearate, said step of adding a first quantity of a resinous compound comprising adding a quantity of a polyacrylic acid polymer to said internal phase, said step of incorporating a chelating agent comprising adding a quantity of ethylenediaminetetraacetic acid to the emulsion, and said equilibrating step comprising adding a quantity of sodium hydroxide to the emulsion.

8. The method as set forth in claim 7, wherein there is included the step of adjusting the pH of said polyacrylic acid to approximately 6.8 before the same is added to said internal phase.

9. A method of killing insects comprising the steps of:

preparing the internal phase of an aqueous emulsion of an unsaturated organic insecticidal compound, said compound being characterized by solubility in a polar solvent, and an absence of the elements iron, copper, zinc and phosphorous, by adding a quantity of said compound along with a quantity of surfactant to an organic polar solvent, said compound being present in a quantity such that the volume of the compound relative to the volume of the subsequently formed emulsion is no more than approximately 4%, and said solvent being present in a quantity such that the volume of the solvent relative to the volume of the subsequently formed emulsion is from 10% to 25%, said surfactant being characterized by the ability to form a microemulsion which is soluble in said polar solvent and said surfactant being present in a quantity of at least approximately two parts by volume of said surfactant to one part by volume of said compound;

diluting said internal phase to at least approximately 70% by volume water to form said emulsion;

adding to the emulsion a quantity of a water soluble resinous compound to comprise at least approximately 0.005% by weight of the subsequently formed microemulsion characterized by the presence of a high number of positive ion accepting sites in each molecule of the resinous compound, there being at least one site in each repeating monomer of the molecule;

incorporating in the emulsion a chelating agent for the calcium ions present in the basil membrane of an insect to increase the penetrability of said insecticidal compound through said insect;

equilibrating said resinous compound with a stoichiometric quantity of a compound capable of donating positive ions to said sites to cause the latter to assume a charge of the same sign as the sign of the charge on the emulsion micelles without substantial change in the pH of the emulison, to increase the charge in the emulsion from the molecules of the resinous compound and thereby effect division of the emulsion micelles into micelles of a smaller size; and applying the equilibrated emulsion to an area where an insect will come into contact therewith.

10. A method of killing insects comprising the steps of:

preparing the internal phase of an aqueous emulsion of an unsaturated organic insecticidal compound, said compound being characterized by solubility in a polar solvent, and an absence of the elements iron, copper, zinc and phosphorous by adding a quantity of said compound along with a quantity of surfactant to an organic polar solvent, said compound being present in a quantity such that the volume of the compound relative to the volume of the subsequently formed emulsion is no more than approximately 4%, and said solvent being present in a quantity such that the volume of the solvent relative to the volume of the subsequently formed emulsion is from 10% to 25%, said surfactant being characterized by the ability to form a microemulsion which is soluble in said polar solvent and said surfactant being present in a quantity of at least approximately two parts by volume of said surfactant to one part by volume of said compound;

diluting said internal phase to at least approximately 70% by volume water to form said emulsion;

incorporating in the emulsion a chelating agent for the calcium ions present in the basil membrane of an insect to increase the penetrability of said insecticidal compound through said instect; and applying said emulsion to an area where an insect will come into contact therewith.

11. A method of increasing the efficacy of an insecticidal compound, wherein said compound is an unsaturated organic compound characterized by solubility in an organic polar solvent and an absence of the elements iron, copper, zinc and phosphorous, said method comprising the steps of:

preparing an aqueous solution of a water soluble polyacrylic acid polymer;

partially equilibrating said polymer with a less than stoichiometric quantity of a base capable of reacting with the carboxyl groups of the polymer to yield water and a substituted polymer molecule;

further equilibrating said polymer with a less than stoichiometric quantity of an amine selected from the group consisting of triamylamine, triethylamine, and di-(2-ethylhexyl)amine;

preparing a solution of said compound by adding a quantity of said compound along with a quantity of surfactant to an organic polar solvent, said compound being present in a quantity such that the volume of the compound relative to the volume of the subsequently formed emulsion is no more than approximately 4%, and said solvent being present in a quantity such that the volume of the solvent relative to the volume of the subsequently formed emulsion is from 10% to 25%, said surfactant being characterized by the ability to form a microemulsion which is soluble in said polar solvent and said surfactant being present in a quantity of at least approximately two parts by volume of said surfactant to one part by volume of said compound; and combining said solutions to form an aqueous emulsion.

12. The method as set forth in claim 11, including the steps of:

adding a saline solution to said emulsion to precipitate a complex comprising said compound and the substituted polymer; and removing said precipitate from the supernatant liquid.

13. The method as set forth in claim 12, wherein there is included the step of drying said precipitate to powder form.

14. The method as set forth in claim 12, wherein the step of preparing the aqueous solution comprises preparing said solution in a concentration of from 0.1 to 0.3% by weight of said polymer.

* * * * *